United States Patent
Peterson et al.

(10) Patent No.: US 7,083,615 B2
(45) Date of Patent: Aug. 1, 2006

(54) SURGICAL TOOL HAVING ELECTROCAUTERY ENERGY SUPPLY CONDUCTOR WITH INHIBITED CURRENT LEAKAGE

(75) Inventors: Alan W. Peterson, Cupertino, CA (US); Scott Manzo, Shelton, CT (US); Frank Mestas, San Francisco, CA (US); Andris Ramans, Sunnyvale, CA (US)

(73) Assignee: Intuitive Surgical Inc, Sunnyvale, CA (US)

( * ) Notice: Subject to any disclaimer, the term of this patent is extended or adjusted under 35 U.S.C. 154(b) by 166 days.

(21) Appl. No.: 10/374,670

(22) Filed: Feb. 24, 2003

(65) Prior Publication Data

US 2004/0167515 A1    Aug. 26, 2004

(51) Int. Cl.
  *A61B 18/12*    (2006.01)
(52) U.S. Cl. .......................................... 606/41; 606/49
(58) Field of Classification Search ............ 606/49–52, 606/41, 45, 1
  See application file for complete search history.

(56) References Cited

U.S. PATENT DOCUMENTS

| 4,360,245 A | * | 11/1982 | Nikitas .................. 439/578 |
| 4,958,539 A | * | 9/1990 | Stasz et al. ............. 76/104.1 |
| 5,207,675 A | * | 5/1993 | Canady .................... 606/40 |
| 5,429,596 A | | 7/1995 | Arias et al. |
| 5,649,956 A | | 7/1997 | Jensen et al. |
| 5,792,135 A | | 8/1998 | Madhani et al. |
| 5,797,900 A | | 8/1998 | Madhani et al. |
| 5,807,378 A | | 9/1998 | Jensen et al. |
| 5,808,665 A | | 9/1998 | Green |
| 5,976,122 A | | 11/1999 | Madhani et al. |
| 6,004,335 A | * | 12/1999 | Vaitekunas et al. ......... 606/169 |
| 6,004,509 A | | 12/1999 | Dey et al. |
| 6,102,909 A | | 8/2000 | Chen et al. |
| 6,132,441 A | | 10/2000 | Grace |
| 6,206,903 B1 | | 3/2001 | Ramans |

(Continued)

FOREIGN PATENT DOCUMENTS

WO    WO 99/50721    10/1999

OTHER PUBLICATIONS

U.S. Appl. No. 09/378,173, filed Aug. 20, 1999.

(Continued)

*Primary Examiner*—Lee S Cohen
*Assistant Examiner*—Aaron Roane
(74) *Attorney, Agent, or Firm*—Townsend and Townsend and Crew

(57) ABSTRACT

The present invention provides improved electrosurgical instruments and systems having electrocautery energy supply conductors that provide inhibited current leakage and methods of performing a robotically controlled minimally invasive surgical procedure while preventing unintended capacitive coupling. A surgical instrument generally comprises an elongate shaft having a proximal end and a distal end and defining an internal longitudinally extending passage. An electrocautery end effector is coupled to or disposed at the distal end of the shaft. An interface or tool base is coupled to or disposed at the proximal end of the shaft and removably connectable to the robotic surgical system. Typically, an independent electrical conductor extends from the interface to the end effector to transmit electrical energy to tissue engaged by the end effector. A sealed insulation tube extends within the passage and over the conductor. A separation is maintained between the sealed insulation tube and the conductor.

28 Claims, 7 Drawing Sheets

U.S. PATENT DOCUMENTS

| | | |
|---|---|---|
| 6,224,593 B1 * | 5/2001 | Ryan et al. ............... 606/41 |
| 6,309,397 B1 * | 10/2001 | Julian et al. ............. 606/130 |
| 6,312,435 B1 | 11/2001 | Wallace et al. |
| 6,331,181 B1 | 12/2001 | Tierney et al. |
| 6,334,860 B1 * | 1/2002 | Dorn ...................... 606/48 |
| 6,394,998 B1 * | 5/2002 | Wallace et al. ............ 606/1 |
| 6,424,885 B1 | 7/2002 | Niemeyer et al. |
| 6,436,107 B1 | 8/2002 | Wang et al. |
| 6,464,701 B1 | 10/2002 | Hooven et al. |
| 6,491,691 B1 | 12/2002 | Morley et al. |
| 6,699,245 B1 * | 3/2004 | Dinger et al. ............. 606/49 |
| 2003/0036748 A1 | 2/2003 | Cooper et al. |

OTHER PUBLICATIONS

U.S. Appl. No. 09/398,507, filed Sep. 17, 1999.
U.S. Appl. No. 09/399,457, filed Sep. 17, 1999.
U.S. Appl. No. 09/626,527, filed Jul. 27, 2000.
U.S. Appl. No. 10/126,451 filed Apr. 18, 2002.
U.S. Appl. No. 10/126,499, filed Apr. 18, 2002.
U.S. Appl. No. 60/111,711, filed Dec. 8, 1998.
U.S. Appl. No. 60/111,713, filed Dec. 8, 1998.
U.S. Appl. No. 60/431,636, filed Dec. 6, 2002.
U.S. Appl. No. 60/285,485, filed Apr. 19, 2001.

* cited by examiner

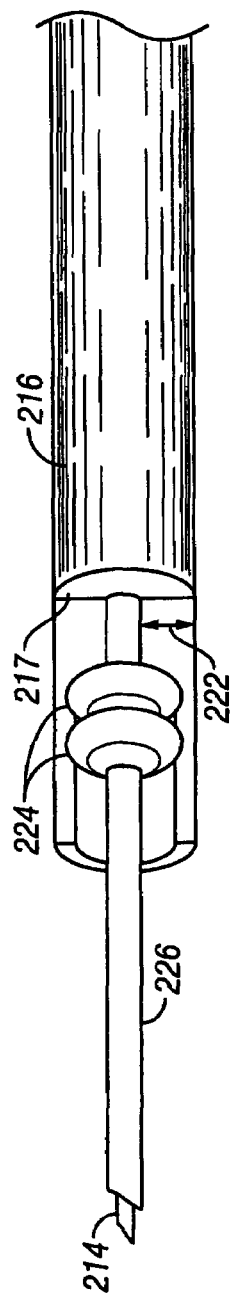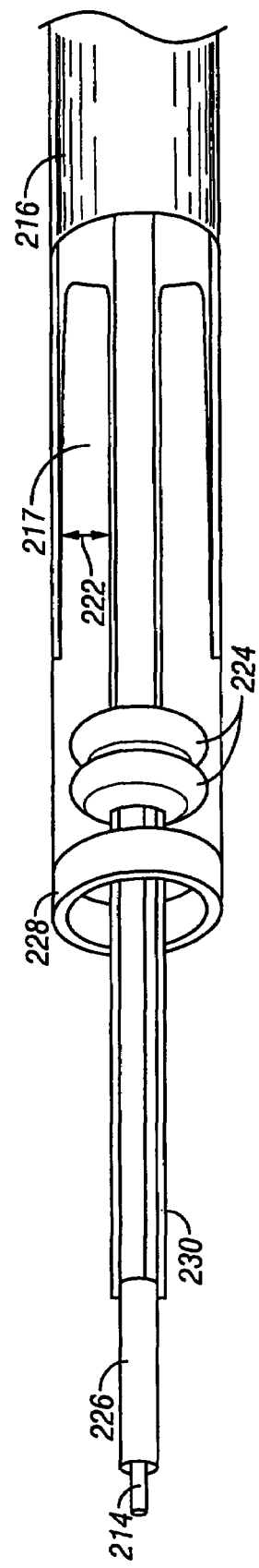
FIG. 5
FIG. 6

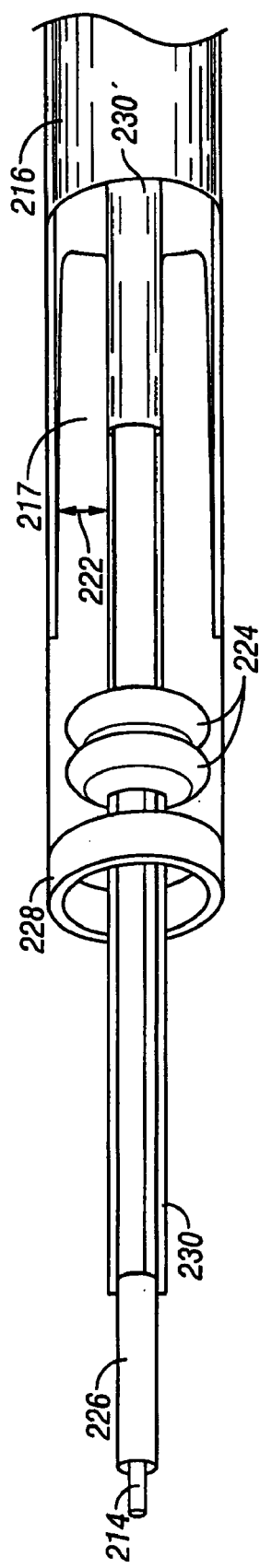
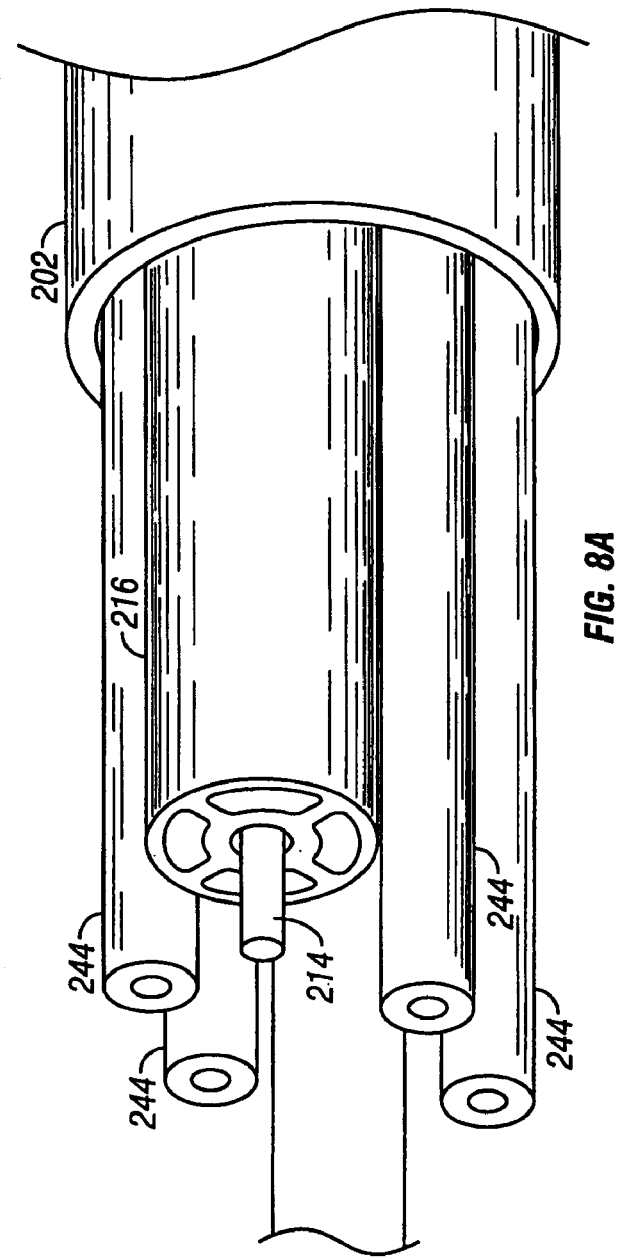
FIG. 7
FIG. 8A

SURGICAL TOOL HAVING ELECTROCAUTERY ENERGY SUPPLY CONDUCTOR WITH INHIBITED CURRENT LEAKAGE

CROSS-REFERENCES TO RELATED APPLICATIONS

This is application is related to the following patents and patent applications, the full disclosures of which are incorporated herein by reference: U.S. patent application Ser. No. 10/726,795; U.S. patent application No. 60/431,636, entitled "Flexible Wrist for Surgical Tool", filed on Dec. 6, 2002; U.S. patent application Ser. No. 10/126,451, entitled "Robotic Tool With Monopolar Electro-Surgical Scissors", filed on Apr. 18, 2002; U.S. patent application Ser. No. 10/187,248, entitled "Surgical Tool Having Positively Positionable Tendon-Actuated Multi-Disk Wrist Joint", filed on Jun. 28, 2002; U.S. Pat. No. 6,491,691, entitled "Minimally Invasive Surgical Hook Apparatus And Method For Using Same", issued Dec. 10, 2002; and U.S. Pat. No. 6,394,998, entitled "Surgical Tools For Use In Minimally Invasive Telesurgical Applications", issued May 28, 2002.

BACKGROUND OF THE INVENTION

The present invention is generally directed to surgical instruments or tools. In particular, the present invention relates to electrosurgical instruments and systems having electrocautery energy supply conductors that provide inhibited current leakage and methods of performing a minimally invasive surgical procedure while preventing unintended capacitive coupling. The surgical instruments can advantageously be used in robotically controlled minimally invasive surgical operations.

Minimally invasive surgical techniques generally reduce the amount of extraneous tissue damage during surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. Patient recovery times, patient discomfort, surgical side effects, and time away from work can also be reduced by increasing the use of minimally invasive surgery.

In theory, a significant number of surgical procedures could potentially be performed by minimally invasive techniques to achieve the advantages just described. However, only a small percentage of procedures currently use minimally invasive techniques as certain instruments, systems, and methods are not currently available in a form for providing minimally invasive surgery.

Traditional forms of minimally invasive surgery typically include endoscopy, which is visual examination of a hollow space with a viewing instrument called an endoscope. One of the more common forms of endoscopy is laparoscopy, which is visual examination and/or treatment of the abdominal cavity. In traditional laparoscopic surgery a patient's abdominal cavity is insufflated with gas and cannula sleeves are passed through small incisions in the musculature of the patient's abdomen to provide entry ports through which laparoscopic surgical instruments can be passed in a sealed fashion. Such incisions are typically about ½ inch (about 12 mm) in length.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by a long extension tube, typically of about 12 inches (about 300 mm) in length, for example, so as to permit the surgeon to introduce the end effector to the surgical site and to control movement of the end effector relative to the surgical site from outside a patient's body.

To perform a surgical procedure, a surgeon typically passes the working tools or instruments through the cannula sleeves to the internal surgical site and manipulates the instruments from outside the abdomen by sliding them in and out through the cannula sleeves, rotating them in the cannula sleeves, levering (i.e., pivoting) the instruments against the abdominal wall, and actuating the end effectors on distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site captured by the laparoscopic camera. Typically, the laparoscopic camera is also introduced through the abdominal wall so as to capture the image of the surgical site. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Although traditional minimally invasive surgical instruments and techniques like those just described have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased use of minimally invasive surgery.

Minimally invasive robotic (or "telesurgical") surgical systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient while viewing the end effector movement on the visual display during the surgical procedure. While typically viewing a three-dimensional image of the surgical site on the visual display, the surgeon performs the surgical procedures on the patient by manipulating master control devices at the remote location, which master control devices control motion of the remotely controlled instruments.

Typically, such a telesurgery system can be provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like. An exemplary robotic surgical system is the DA VINCI™ system available from Intuitive Surgical, Inc. of Sunnyvale, Calif.

A typical electrosurgical treatment instrument is capable of treating tissue of an organism with the use of heat produced by electrical energy. The instrument typically includes an electrode or cautery hook that applies current to living tissue at a surgical site. Optionally, the instrument may comprise a combined cutting, shearing, clamping, stapling, or grasping electrosurgical instrument. As the tissue current is conducted through the tissue, the tissue temperature rises, ultimately causing desiccation, cutting, cauterization, and/or coagulation of the target tissue (i.e., blood vessels and the like). While such electrocautery instruments provide significant advances in minimally invasive surgical technology, some shortcomings still need to be addressed.

In particular, high voltage current may unintentionally leak from an electrocautery supply conductor that delivers electrical energy to an end effector (e.g., electrode) during a treatment procedure. This is especially a problem if fluids, such as blood or saline, enter or seep into an interior of an instrument shaft that houses the conductor due to shaft pressurization. Such seepage may cause increased capacitive coupling between the instrument shaft and a patient resulting in unintended current voltage being imparted to the patient. Conduction only at a tip of the end effector to the target tissue is desirable. Conduction by increased capacitive coupling is undesirable as it may cause unnecessary and unintended burning of the patient from the tool shaft. Furthermore, such increased capacitive coupling may be passed along the instrument and cause melting or burning of the surgical tool itself. Also, in the case of robotic surgical systems, which are of particular interest to the present invention, such increased capacitive coupling may be passed along the instrument to the telesurgical system in general causing damage to such a system, especially sensitive electronics. Another disadvantage is that high voltage current may unintentionally creep to an exterior surface of an exposed wrist-like mechanism which is provided between the end of the shaft and the end effector. In particular, fluid such as blood or saline may arc over the wrist surface from the conducting end effector tip and cause wrist surface conduction. Such wrist surface conduction in turn may also cause unintended burning of the patient and/or melting of the wrist mechanism.

Therefore, it would be desirable to provide improved electrosurgical instruments and systems having electrocautery energy supply conductors that provide inhibited current leakage and methods of performing a minimally invasive surgical procedure while preventing unintended capacitive coupling. It would be further desirable if such electrosurgical instruments, systems, and methods inhibit wrist surface conduction. The electrosurgical instruments should also be compatible with minimally invasive robotic surgical systems. At least some of these objectives will be met by the inventions described hereinafter.

BRIEF SUMMARY OF THE INVENTION

The present invention is generally directed to surgical instruments or tools. In particular, the present invention relates to improved electrosurgical instruments and systems having electrocautery energy supply conductors that provide inhibited current leakage and methods of performing a minimally invasive surgical procedure while preventing unintended capacitive coupling. Such electrosurgical instruments, systems, and methods also inhibit wrist surface conduction. The electrosurgical instruments can advantageously be used in robotically controlled minimally invasive surgical operations.

In a first aspect of the present invention, a surgical instrument for use with a minimally invasive robotic surgical system may comprise an elongate shaft having a proximal end and a distal end and defining an internal longitudinally extending passage. An electrocautery end effector is coupled to or disposed at the distal end of the shaft. An interface or tool base is coupled to or disposed at the proximal end of the shaft and removably connectable to the robotic surgical system. Typically, an independent electrical conductor extends from the interface to the end effector to transmit electrical energy to tissue engaged by the end effector. A sealed insulation tube extends within the passage and over the conductor. A separation is maintained between the sealed insulation tube and the conductor.

The insulation tube and separation of the present invention are particularly advantageous as such a structure increases a dielectric resistance so as to inhibit capacitive coupling between the shaft and a surgical patient. This in turn inhibits unintentional current leakage from the conductor to non-target tissue during a treatment procedure, even in cases where fluids, such as blood or saline, seep into an interior of the shaft due to shaft or patient body pressurization. As such, conduction of the current is limited at a tip of the end effector to the treatment tissue. Moreover, unintended and unnecessary burning of the patient, collateral tissue damage, and the like from the tool shaft is minimized as the insulation tube and separation inhibit current leakage from the shaft to the patient. Potential damage to the instrument, such as burning or melting, and/or the robotic surgical system, such as shorting of sensitive electronics, is also minimized with the present invention which decreases the possibility for capacitive conduction being passed along the instrument itself and/or to the robotic system.

The structural material and/or geometrical properties of the insulation tube and separation provide the increased dielectric resistance which decreases the capacitive conduction from the conductor. In a preferred embodiment, the separation may comprise a low dielectric constant material. The low dielectric constant material may be a separate component or structure of the instrument or may preferably form an integrated unit with the sealed insulation tube. Suitable low dielectric materials include fluorinated ethylene propylene, polyimide, silicone, polytetrafluoroethylene, tetrafluoroethylene, perfluoroalkoxy, ethylene tetrafluoroethylene, polypropylene, or a combination thereof. Fluorinated ethylene propylene is a preferred material for its low cost and ease of manufacturability. In a second preferred embodiment, the separation may comprise air, i.e., no filling at all. The insulation tube may form a geometry that seals a concentric ring of air around the conductor. Still further, the insulation tube may form a geometry that seals a plurality of sectors of air around the conductor. In any embodiment, a radial separation distance of the conductor from the insulation tube is maximized to the geometrical constraints of the shaft or until a threshold current leakage is attained, generally being in the range from about 1/64 inch to about 3/32 inch. Such structural and material properties of the insulation tube and separation can reduce capacitive coupling by about 40% to about 75% over a similar instrument lacking the insulation tube and separation. Moreover, a reduction in capacitive coupling may result in the current leakage between the shaft and the patient to be limited to a range from about 20 mA to about 35 mA.

The insulation tube will generally comprise a hypotube, typically a hollow tube, having a cross-sectionally circular profile. The insulation tube will generally be dimensioned to have an outer diameter in the range from about 1/32 inch to about 3/16 inch, preferably from about 1/16 inch to about 3/16 inch, more preferably having a diameter of about 1/8 inch, and a length in the range from about 12 inches to about 18 inches. Suitable materials for the insulation tube include non-conductive materials such as fluorinated ethylene propylene, polyimide, silicone, polytetrafluoroethylene, tetrafluoroethylene, perfluoroalkoxy, ethylene tetrafluoroethylene, polypropylene, or a combination thereof. Fluorinated ethylene propylene is a preferred material for its low cost and ease of manufacturability. Polyimide is also another preferred material, especially when the separation comprises air, as it further increases dielectric resistance. Polyimide is also a thin material (so as to maximize the radial separation distance) that still provides sufficient stiffness, is sleek so as to not cause any friction with other cables housed within the shaft, and allows for the adhesion of sealants, as described in more detail below.

The sealed insulation tube may further comprise seals, such as o-rings, heat shrink seals, and the like, located between proximal and distal ends of the insulation tube and the conductor. The seals advantageously center the conductor within the insulation tube and thereby maximize the radial separation distance of the conductor from the insulation tube, particularly when the separation comprises air. The seals may be separate components or be formed integrally with the insulation tube. The seal preferably comprise two pairs of o-rings, a first pair positionable at a proximal end of the insulation tube and a second pair positionable at a distal end of the insulation tube. The sealed insulation tube will typically have a pressure threshold in the range from about −15 psi to 30 psi for resisting fluid leakage as well as bursting during sterilization or cleaning i.e., autoclaving, of the instrument. Further, the sealed insulation tube may comprise an o-ring or heat shrink seal positionable at a center of the insulation tube to further help center the conductor within the insulation tube as well as prevent crimping, slacking, or bending of the conductor.

The surgical instrument may further comprise a second insulative tubing disposed over the conductor and extending at least within a length of the sealed insulation tube. Suitable materials for the second tubing include non-conductive materials such as fluorinated ethylene propylene, polyimide, silicone, polytetrafluoroethylene, tetrafluoroethylene, perfluoroalkoxy, ethylene tetrafluoroethylene, polypropylene, or a combination thereof. In some instances, the second tubing may extend within an entire length of the sealed insulation tube so as to form a dual insulation tube assembly. Seals may additionally be positionable between proximal and distal ends of the second tubing and the conductor and/or the second tubing and the insulation tube. The second tubing helps prevent bending or slacking of the conductor as well as helps to maintain the conductor within the center of the insulation tube. Moreover, the second tubing may provide extra security for securing the conductor to the sealing mechanisms. Additionally, the non-conductive material forming the second tubing may further enhance the dielectric resistance of the insulation tube and separation.

The conduction assembly described above advantageously provides electrosurgical treatment in a safe effective manner that minimizes current leakage. The present invention further incorporates additional safety features to further prevent current leakage to non-target tissue so at reduce unwanted and unintended burning of the patient, collateral tissue damage, or the like. In particular, an insulative sheath may be disposed over the conductor. It will be appreciated that such a thin insulative sheath or jacket is sufficient to effectively inhibit DC current, but is not sufficient in and of itself to substantially reduce RF current leakage due to capacitive coupling. Additionally or alternatively, the elongate shaft may be covered with an insulating material.

The electrocautery end effector for delivering electrical energy to treatment tissue is disposed on the distal end of the shaft. The end effector may be removably coupleable to the shaft to conveniently permit the end effector to be easily mounted and de-mounted, e.g., for replacement or refurbishing, or may be permanently mounted or connected to the shaft. Preferably, the end effector comprises an electrode or cautery hook. Optionally, the end effector may comprise an electrosurgical scalpel, blade, scissor, grasper, clamp, stapler, and the like. The electrocautery end effector and at least distal end of the shaft are insertable and retractable through a minimally invasive surgical incision. The surgical instrument interface may further comprise an electrical connector for connecting the conductor to an external electrosurgical generator.

The surgical instrument may further comprise a wrist member defining an end effector pivot and a wrist pivot spaced apart from the end effector pivot. The end effector is pivotally connected at the end effector pivot. The wrist member is pivotally mounted on the distal end of the shaft by means of the wrist pivot to be angularly displaceable relative to the shaft about a wrist pivot axis defined by the wrist pivot. Alternatively, the wrist member may comprise a non-pivot wrist mechanism which is described in more detail in related co-pending U.S. patent application Ser. No. 60/431,636, entitled "Flexible Wrist for Surgical Tool", and U.S. patent application Ser. No. 10/187,248, entitled "Surgical Tool Having Positively Positionable Tendon-Actuated Multi-Disk Wrist Joint". Typically, such a wrist member includes a movable portion coupleable to the end effector and to the distal end of the shaft, the movable portion being actuatable to move the end effector in at least one degree of freedom relative to the shaft. The movable portion may include a plurality of pivotally coupled segments. In other embodiments, the movable portion may include at least one resilient element coupling the end effector to the distal end of the shaft. Significantly, at least a portion of the wrist, preferably a distal portion, is formed from a natural ULTEM™ material or a fluoropolymer so as to inhibit wrist surface conduction. As such, undesirable high voltage current that may creep to an exterior surface of the exposed wrist member causing wrist surface conduction will be inhibited by the non-conducting natural ULTEM™ material wrist thereby minimizing unintended burning of the patient and/or melting of the wrist mechanism.

In a second aspect of the present invention, a surgical instrument for use with a robotic surgical system may comprise an elongate shaft having a proximal end and a distal end and defining an internal longitudinally extending passage. The distal end of the shaft is configured to permit insertion through a minimally invasive incision in a body of a patient. An electrocautery end effector is disposed at the distal end of the shaft. An interface is disposed at the proximal end of the shaft and removably connectable to the robotic surgical system. A conductor extends from the interface and electrically communicates with at least a portion of the end effector so as to deliver electrical energy to tissue engaged by the end effector. An insulative sleeve is disposed over the conductor. A sealed insulation tube extends within the passage and over the insulated conductor. A separation is maintained between the sealed insulation tube and the insulated conductor, the separation comprising a low dielectric constant material. The instrument further includes at least one o-ring between the insulation tube and the insulated conductor. Preferably, the instrument includes two o-rings, wherein a first o-ring is positionable at a proximal end of the insulation tube and a second o-ring is positionable at a distal end of the insulation tube.

In a third aspect of the present invention, a robotical surgical system may comprise a robotic arm having an instrument holder. An electrocautery instrument is detachably mountable on the instrument holder. The electrocautery instrument comprises a proximal portion for engaging the instrument holder, an elongate shaft extending from the proximal portion to a distal end and defining an internal longitudinally extending passage, and an electrocautery end effector coupleable to the distal end of the shaft. A conductor electrically communicates with at least a portion of the end effector so as to deliver electrical energy to tissue engaged by the end effector. The conductor is coupled to an electrical connector on the proximal portion. A sealed insulation tube extends within the passage and over the conductor. A separation is maintained between the sealed insulation tube and the conductor. An electrosurgical generator is detachably connected to the connector of the proximal portion so as to transmit electrosurgical energy to the electrocautery end effector.

In a fourth aspect of the present invention, methods for performing minimally invasive robotic surgical procedures with the electrosurgical instruments described above are provided. One method includes connecting a surgical instrument to a robotic surgical system, the surgical instrument having an elongate shaft, at one end of which an electrocautery end effector is disposed. The end effector is positioned with the robotic surgical system through an entry port in a patient body and in contact with tissue at a surgical site. Electrical energy is delivered to tissue engaged by the end effector while preventing unintended capacitive coupling between the shaft and the patient. Delivering electrical energy may comprise transmitting electrical energy to the end effector from a conductor. The conductor is housed within a sealed insulation tube extending within the elongate shaft, wherein a separation is maintained between the sealed insulation tube and the conductor. As described above, the sealed insulation tube and separation increase a dielectric resistance.

In a fifth aspect of the present invention, an electrosurgical instrument for use with a minimally invasive surgical system (e.g., robotic or manually-performed endoscopic system) is provided. The instrument may comprises an elongate shaft having a proximal end and a distal end and defining an internal longitudinally extending passage. An electrocautery end effector is disposed at the distal end of the shaft, wherein at least the end effector and distal end of the shaft are configured to be insertable through a minimally invasive surgical incision. A user-controllable interface is disposed at the proximal end of the shaft. A conductor extends from the interface to the end effector so as to deliver electrical energy to tissue engaged by the end effector. A sealed insulation tube extends within the passage and over the conductor, wherein a separation is maintained between the sealed insulation tube and the conductor. The user-controllable interface may be configured to couple to a manually movable handle or may be configured to removably couple to a servomechanical tool holder of a robotic surgical system.

A further understanding of the nature and advantages of the present invention will become apparent by reference to the remaining portions of the specification and drawings.

BRIEF DESCRIPTION OF THE DRAWINGS

FIG. 5 is an exploded schematic sectional side view of a first embodiment of the sealed insulation tube of FIG. 4.

FIG. 6 is an exploded schematic sectional side view of a second embodiment of the sealed insulation tube of FIG. 4.

FIG. 7 is an exploded schematic sectional side view of a third embodiment of the sealed insulation tube of FIG. 4.

FIGS. 8A–8C are exploded schematic side and cross sectional views of a fourth embodiment of the sealed insulation tube of FIG. 4.

DETAILED DESCRIPTION OF THE INVENTION

The present invention provides apparatus, systems, and methods for use in robotically controlled minimally invasive surgical operations. In particular, the present invention relates to improved electrosurgical instruments and systems having electrocautery energy supply conductors that provide inhibited current leakage and methods of performing a minimally invasive surgical procedure while preventing unintended capacitive coupling. Such electrosurgical instruments, systems, and methods also inhibit wrist surface conduction. The conduction assembly advantageously provides electrosurgical treatment in a safe and effective manner by incorporating a variety of safety features to prevent current leakage so as to reduce unwanted and unintended burning of the patient, collateral tissue damage, melting of the instrument, damage to the robotic surgical system, or the like.

Generally, the electrosurgical instruments of the present invention are capable of treating tissue of an organism with the use of heat produced by electrical energy. The instruments typically include an electrode or cautery hook that applies current to living tissue at a surgical site. Optionally, the instrument may comprise a combined cutting, shearing, clamping, stapling, or grasping electrosurgical instrument. As the tissue current is conducted through the tissue, the tissue temperature rises, ultimately causing desiccation, cutting, cauterization, and/or coagulation of the treatment tissue (i.e., blood vessels and the like). The electrosurgical treatment may further reduce bleeding of tissue by cauterizing tissue and coagulating blood, or achieve various other desired effects on the treatment tissue.

Figure 1:
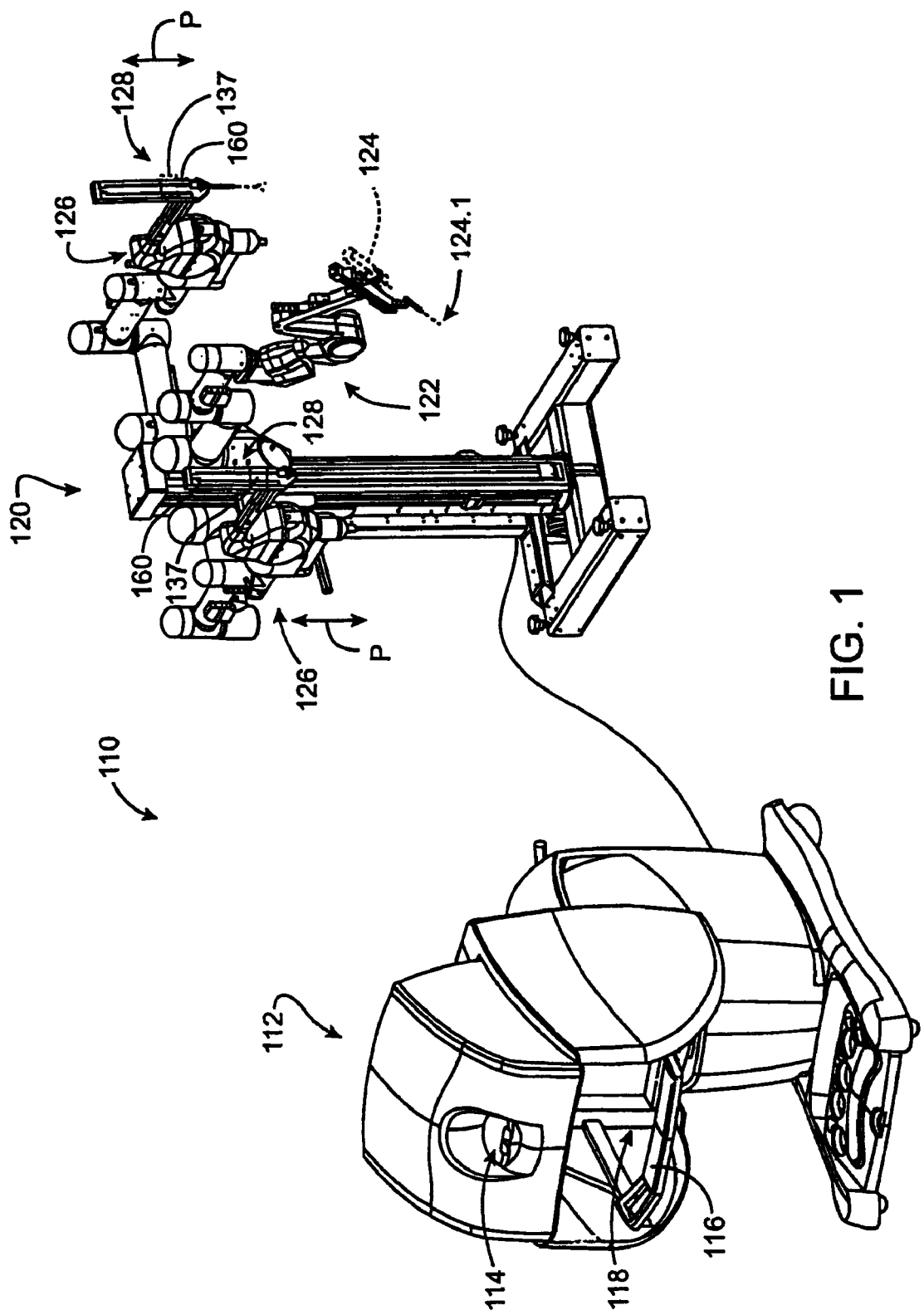
FIG. 1 is a perspective illustration of a robotic surgical system with which various embodiments of the present invention may be used.

Referring now to FIG. 1, a robotic surgical system 110 generally includes a user-operated control station or "surgeons console" 112 and a surgical work station or "cart" 120. The control station 112 includes an image display module 114 for displaying an image of a surgical site, a support 116 on which an operator may rest his/her forearms, and a space 118 where two master control devices are located (not shown). When using control station 112, a surgeon or other user typically sits in a chair in front of control station 112, views the surgical site through the display module 114, and grips the master controls one in each hand while resting the forearms on support 116. An exemplary robotic surgical system as described in FIG. 1 is the DA VINCI™ system available from Intuitive Surgical, Inc. of Sunnyvale, Calif.

Control station 112 is generally coupled to cart 120 such that commands from the master controls may be transmitted to the cart 120. In use, cart 120 is positioned adjacent a patient requiring surgery and is then normally caused to remain stationary until a surgical procedure to be performed by means of surgical system 110 has been completed. Cart 120 typically has wheels or castors to render it mobile. Control station 112 is typically positioned remote from cart 120 and in some embodiments may be separated from cart 120 by a great distance, for example miles away, but will typically be used within an operating room with the cart 120.

In various embodiments, cart 120 includes at least three robotic arm assemblies 122, 126, 126, one of which is configured to hold an image capture device 124 and the others of which are configured to hold surgical instruments 128. Alternatively, the cart may include more or fewer than three robotic arm assemblies and the robotic arm assemblies may be configured to hold any suitable tool, instrument, imaging device and/or the like. Image capture device 124 may include any suitable device, such as an endoscope, fiber optic camera, or the like. Image capture device 124 generally includes an object viewing end 124.1 at a remote end of an elongate shaft configured to enable the viewing end 124.1 to be inserted through an entry port in a patient's body to capture an image of the surgical site.

Coupling of cart 120 to control station 112 generally enables display module 114 to display an image captured by image capture device 124. Coupling of cart 120 to control station 112 also typically allows each of the master controls on the control station 112 (not shown) to control one robotic arm assembly 126 and one surgical instrument 128. In various embodiments, each master control may alternatively be used to control more than one robotic arm assembly 126 and/or more than one surgical instrument 128.

Surgical instruments 128 on the robotic arm assemblies 126 typically include elongate shafts, with proximal and distal ends. End effectors are generally mounted on wrist-like mechanisms pivotally mounted on the distal ends of the shafts, for enabling the instruments 128 to perform one or more surgical tasks. Generally, the elongate shafts of surgical instruments 128 allow the end effectors to be inserted through entry ports in a patient's body so as to access the internal surgical site. Movement of the end effectors is generally controlled via master controls on the control center 112.

Figure 2:
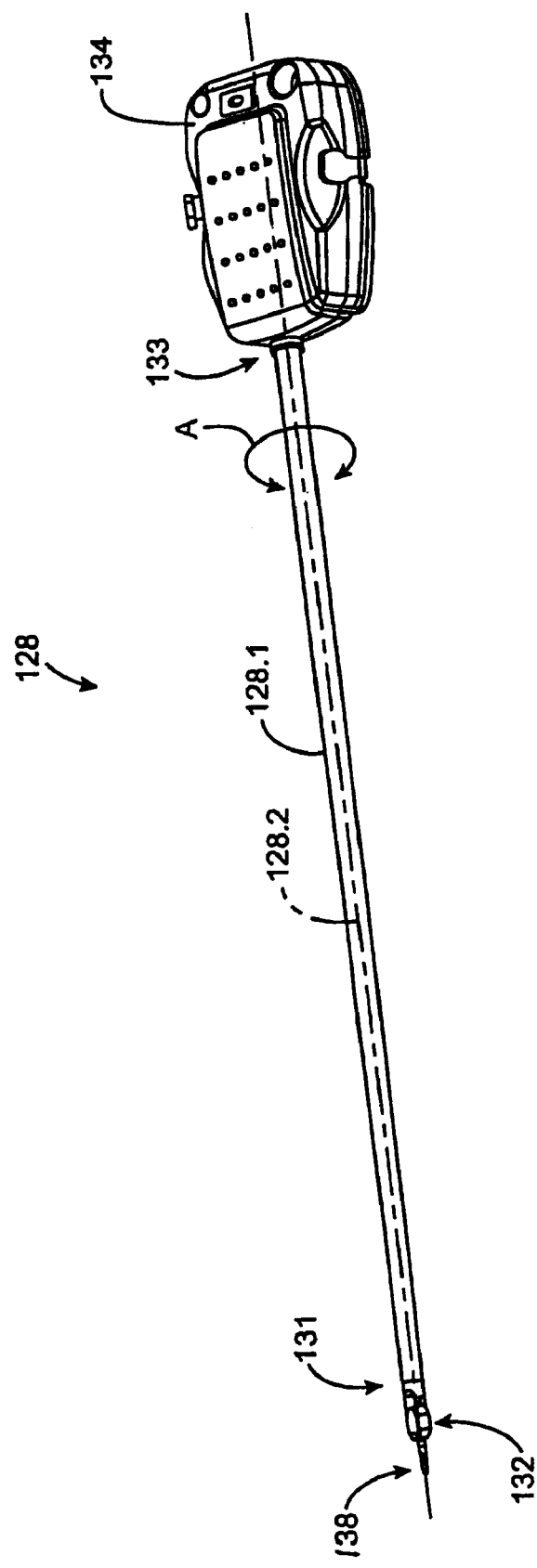
FIG. 2 is a perspective illustration of a robotic surgical tool which may be used with the robotic surgical system of FIG. 1.

Referring now to FIG. 2, surgical instrument 128 generally includes an elongate shaft 128.1 having a proximal end 133 and a distal end 131, a pivot 132, an end effector 138 disposed at the distal end, and an instrument base 134 disposed at the proximal end. Base 134 is generally configured to releasably engage an interface member of the robotic surgical system, such as robotic surgical system 110 in FIG. 1. In general, instrument 128 is engaged with the system via base 134 (base not shown in FIG. 1) such that instrument 128 is releasably mountable on a carriage 137 which can be driven to translate along a linear guide formation 160 of the arm 126 in the direction of arrows P.

Figure 3:
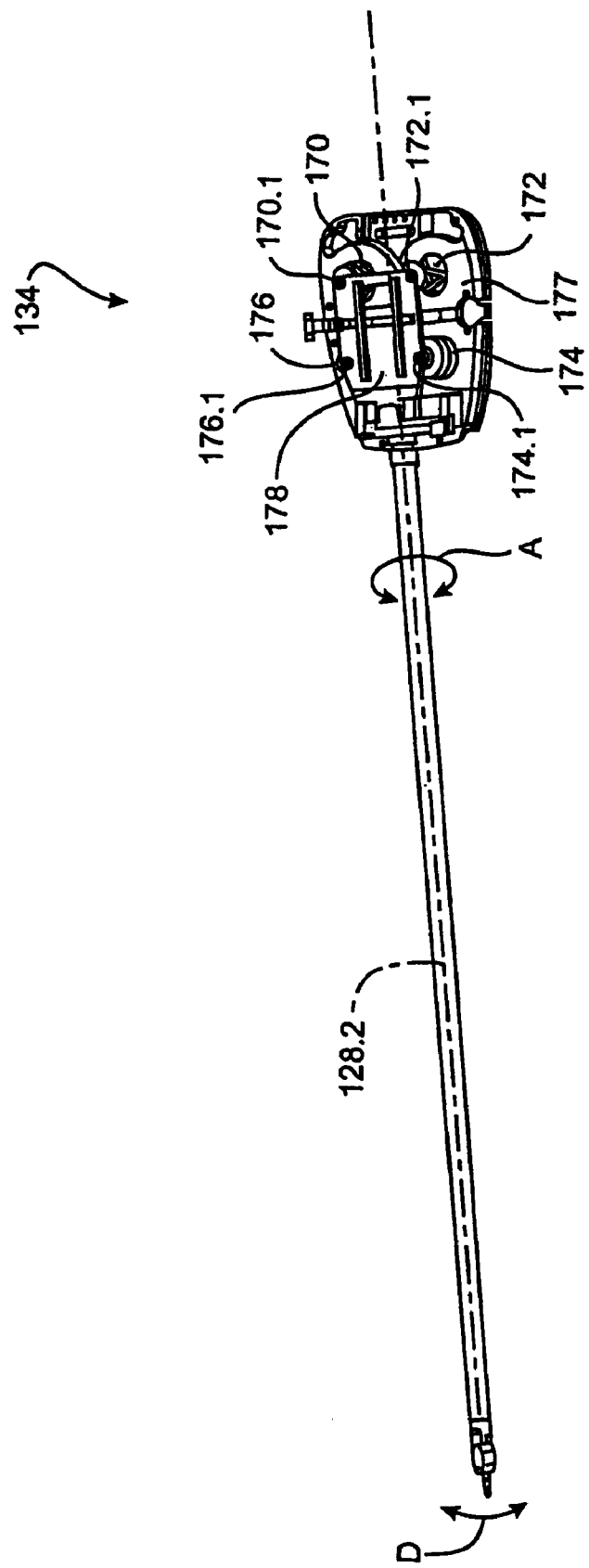
FIG. 3 is a perspective illustration of the robotic surgical tool in FIG. 2, with a cover of a tool base removed to show internal structures of the tool base.

With reference to FIGS. 2 and 3, shaft 128.1 is rotatably mounted on base 134 for rotation about an axis 128.2 extending longitudinally along the shaft 128.1 as indicated by the arrows A. Thus, when mounted on an arm assembly 126, end effector 138 may have a plurality of degrees of freedom of movement relative to manipulator arm 126, in addition to actuation movement of the end effector itself, The instrument may be translated along an insertion axis (Arrows P in FIG. 1). Typically, the instrument degrees of freedom include rotation about the axis 128.2 as indicated by arrows A, and in the case of instruments 128 including pivots 132, angular displacement as a whole about pivot 132 as indicated by arrow D. Alternatively, the distal pivoting degree of freedom may be omitted. A single pivot wrist, a multi-pivot wrist, a distal roll joint mechanism, or other joints or wrist-like mechanisms may be included to provide additional operational degrees of freedom to the end effector. Movement of end effector 138 relative to manipulator arm 126 controlled by appropriately positioned actuators, such as electric motors, or the like, which respond to inputs from an associated master control at the control station 112, so as to drive the end effector 138 to a required orientation as dictated by movement of the associated master control.

Referring now to FIG. 3, base 134 of surgical instrument 128 suitably includes transmission members 170, 172, 174, and 176, which include spools secured on shafts 170.1, 172.1, 174.1, and 176.1. Ends of shafts 170.1, 172.1, 174.1, 176.1 generally extend from a side 177 of base 134 to a mounting plate 178 within base 134 and are configured to rotate. Generally, the ends of shafts 170.1, 172.1, 174.1, 176.1 at side 177 of base 134 extend through side 177, to an outer surface of side 177 (not shown). At the outer surface, each shaft 170.1, 172.1, 174.1, 176.1 includes an engaging member (not shown) configured to releasably couple with a complementary engaging member (not shown) rotatably mounted on the carriage 137 of a robotic arm assembly 126 (see FIG. 1). The engaging members on carriage 137 are generally coupled to actuators (not shown), such as electric motors or the like, to cause selective angular displacement of each engaging member on the carriage 137 in response to actuation of its associated actuator. Thus, selective actuation of the actuators is transmitted through the engaging members on the carriage 137, to the engaging members on the opposed ends of the shafts 170.1, 172.1, 174.1, 176.1 to cause selective angular displacement of the spools 170, 172, 174, 176. Where more or fewer degrees of freedom are desired, the number of spools may be decreased or increased.

Figure 4:
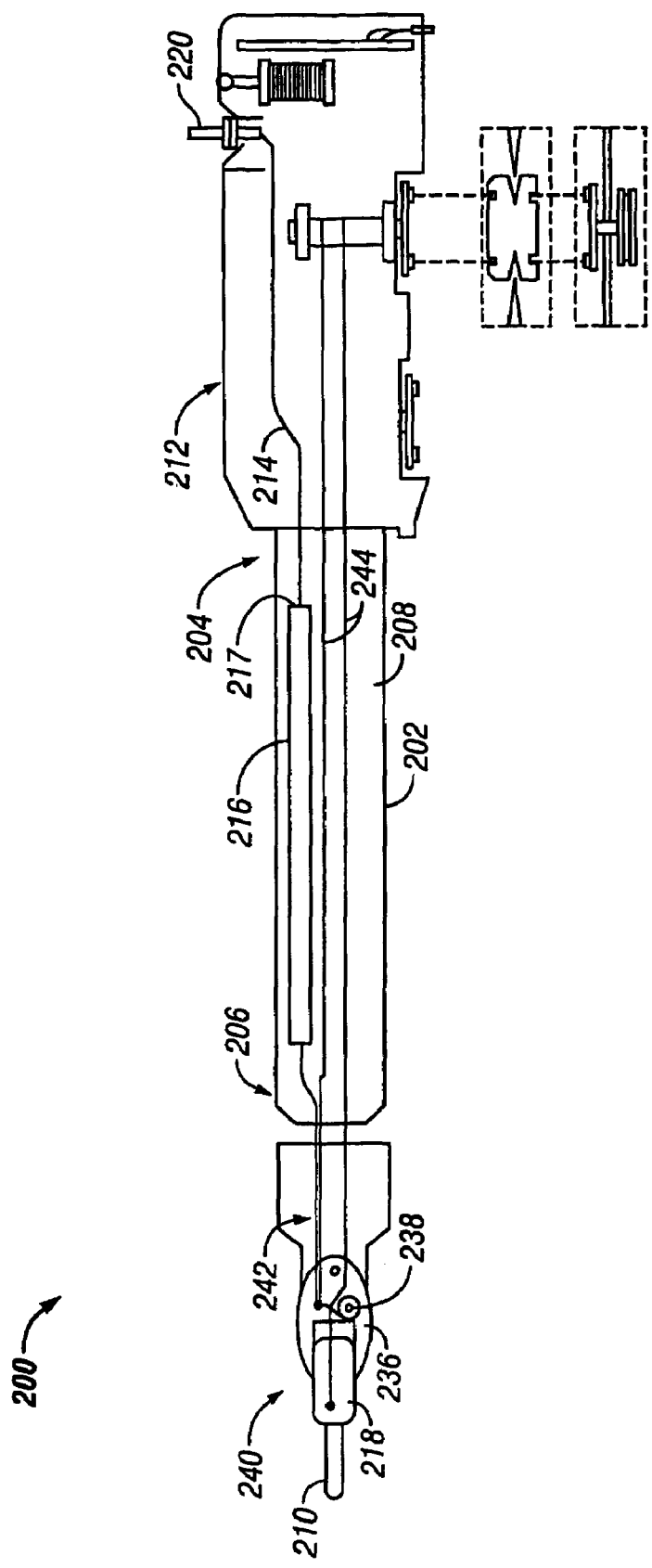
FIG. 4 is a schematic side view of an exemplary electrosurgical instrument constructed in accordance with the principles of the present invention.

Referring now to FIG. 4, a schematic side view of an exemplary electrosurgical instrument 200 constructed in accordance with the principles of the present invention is illustrated. The instrument 200 is in a form generally similar to that shown in FIG. 3. The surgical instrument 200 for use with a minimally invasive robotic surgical system 110 may comprise an elongate shaft 202 having a proximal end 204 and a distal end 206 and defining an internal longitudinally extending passage 208. An electrocautery end effector 210 is coupled to or disposed at the distal end 206 of the shaft 202. An interface or tool base 212 is coupled to or disposed at the proximal end 204 of the shaft 202 and removably connectable to the robotic surgical system 110. Typically, an independent electrical conductor 214 extends from the interface 212 to the end effector 210 to transmit electrical energy to tissue engaged by the end effector 210. A sealed insulation tube 216 extends within the passage 208 and over the conductor 214. A separation 217 is maintained between the sealed insulation tube 216 and the conductor 214. The following depictions are for illustration purposes only and do not necessarily reflect the actual shape, size, or dimensions of the robotic electrosurgical instrument 200.

With reference to FIGS. 5–8C, various embodiments of the sealed insulation tube are illustrated. It will be appreciated that irrespective of which particular embodiment is chosen, the insulation tube 216 and separation 217 in general are particularly advantageous as such structures increase a dielectric resistance so as to inhibit capacitive coupling between the shaft 202 and a surgical patient. This in turn inhibits unintentional current leakage from the conductor 214 to non-target tissue during a treatment procedure, even in cases where fluids, such as blood or saline, seep into an interior 208 of the shaft 202 due to shaft or patient body pressurization. As such, conduction of the current is limited at a tip of the end effector 210 to the treatment tissue. Moreover, unintended and unnecessary burning of the patient, collateral tissue damage, and the like from the tool shaft is minimized as the insulation tube 216 and separation 217 inhibit current leakage from the shaft 202 to the patient. Potential damage to the instrument 200, such as burning or melting, and/or the robotic surgical system 110, such as shorting of sensitive electronics, is also minimized with the present invention which decreases the possibility for capacitive conduction being passed along the instrument itself and/or to the robotic system. The structural material and/or geometrical properties of the insulation tube 216 and separation 217 provide the increased dielectric resistance which decreases the capacitive conduction from the conductor 214.

Referring now to FIG. 5, in a first preferred embodiment the separation 217 may comprise a low dielectric constant material. As shown, the low dielectric constant material 217 forms an integrated unit with the sealed insulation tube 216. Suitable low dielectric materials include fluorinated ethylene propylene, polyimide, silicone, polytetrafluoroethylene, tetrafluoroethylene, perfluoroalkoxy, ethylene tetrafluoroethylene, polypropylene, or a combination thereof. Fluorinated ethylene propylene is a preferred material for its low cost and ease of manufacturability. A radial separation distance 222 of the conductor 214 from the insulation tube 216 is maximized to the geometrical constraints of the shaft 202 or until a threshold current leakage is attained, generally being in the range from about 1/64 inch to about 3/32 inch. Such structural and material properties of the insulation tube 216 and separation 217 can reduce capacitive coupling by about 40% to about 75% over a similar instrument lacking the insulation tube and separation. Moreover, a reduction in capacitive coupling may result in the current leakage between the shaft and the patient to be limited to a range from about 20 mA to about 35 mA with 50 watts of power applied to the surgical instrument and measured across a 100 ohm resistor.

The insulation tube 216 will generally comprise a hypotube, typically a hollow tube, having a cross-sectionally circular profile. The insulation tube 216 will generally be dimensioned to have an outer diameter in the range from about 1/32 inch to about 3/16 inch, preferably from about 1/16 inch to about 3/16 inch, and more preferably having a diameter of about 1/8 inch, and a length in the range from 12 inches to about 18 inches. Such dimensions are maximized to the geometrical constraints of the shaft 202 or until a threshold current leakage is attained. Suitable materials for the insulation tube 216 include non-conductive materials such as fluorinated ethylene propylene, polyimide, silicone, polytetrafluoroethylene, tetrafluoroethylene, perfluoroalkoxy, ethylene tetrafluoroethylene, polypropylene, or a combination thereof. Fluorinated ethylene propylene is a preferred material for its low cost and ease of manufacturability.

The sealed insulation tube 216 may further comprise seals 224, such a pair of o-rings, located between proximal and distal ends of the insulation tube 216 and the conductor 214. The seals 224 advantageously center the conductor 214 within the insulation tube 216 and thereby maximize the radial separation distance 222 of the conductor 214 from the insulation tube 216. The seals 224 may comprise separate structures, wherein a first pair is positionable at a proximal end of the insulation tube 216 and a second pair is positionable at a distal end of the insulation tube 216. The sealed insulation tube 216 will typically have a pressure threshold in the range from about −15 psi to 30 psi for resisting fluid leakage as well as bursting during sterilization or cleaning i.e., autoclaving, of the instrument.

The conduction assembly described above advantageously provides electrosurgical treatment in a safe effective manner that minimizes current leakage. The present invention further incorporates additional safety features to further prevent current leakage to non-target tissue so at reduce unwanted and unintended burning of the patient, collateral tissue damage, or the like. In particular, an insulative sheath 226 may be disposed over the conductor 214, such as a polytetrafluoroethylene or TEFLON™ material. Additionally or alternatively, the elongate shaft 202 may be covered with an insulating material or be made entirely from non-conductive materials. Suitable insulative materials include polymeric materials such as Polymed II and ULTEM™ material.

Referring now to FIGS. 6 and 7, second and third preferred embodiments of the insulation tube 216 are illustrated. In these embodiments, the separation 217 comprises air, i.e., no filling at all. The insulation tube 216 may form a geometry that seals a concentric ring of air around the conductor 214. In such an embodiment, polyimide is the preferred material for the insulation tube 216 as it further increases dielectric resistance. Polyimide is also a thin material (so as to maximize the radial separation distance 222) that still provides sufficient stiffness, is sleek so as to not cause any friction with other cables 244 housed within the shaft, and allows for the adhesion of seals 224. Moreover a ULTEM™ material fitting 228 is provided distal and proximal of the o-ring pair 224.

With reference to FIG. 6, the surgical instrument 200 may further comprise a second insulative tubing 230 disposed over the conductor 214 and extending at least within a length of the sealed insulation tube 216. Suitable materials for the second tubing 230 include non-conductive materials such as fluorinated ethylene propylene, polyimide, silicone, polytetrafluoroethylene, tetrafluoroethylene, perfluoroalkoxy, ethylene tetrafluoroethylene, polypropylene, or a combination thereof. In some instances, the second tubing 230 may be formed from fluorinated ethylene propylene and extend all the way through a proximal section of a wrist-like mechanism, which is described in more detail below. With reference to FIG. 7, the second tubing 230' may be formed form polyimide and extend within an entire length of the sealed insulation tube 216 so as to form a dual insulation tube assembly. The second tubing 230, 230' helps prevent bending or slacking of the conductor 214 as well as helps to maintain the conductor 214 within the center of the insulation tube 216. Moreover, the second tubing 230, 230' may provide extra security for securing the conductor 214 to the sealing mechanisms 228. Additionally, the non-conductive material forming the second tubing 230, 230' may further enhance the dielectric resistance of the insulation tube 216 and separation 217.

Figure 8B:
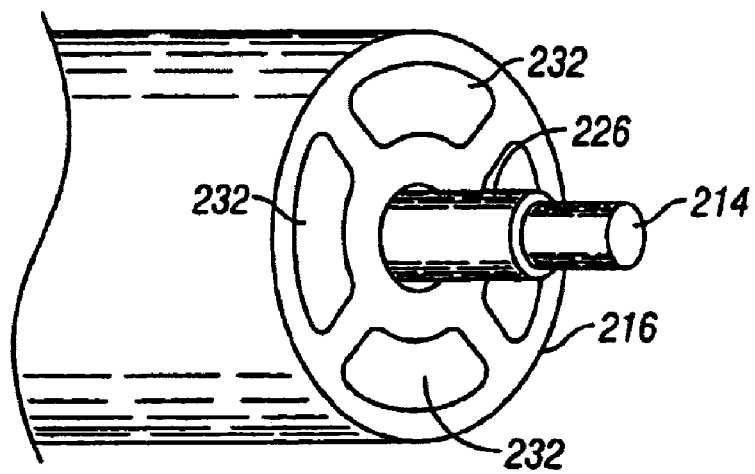
Figure 8C:
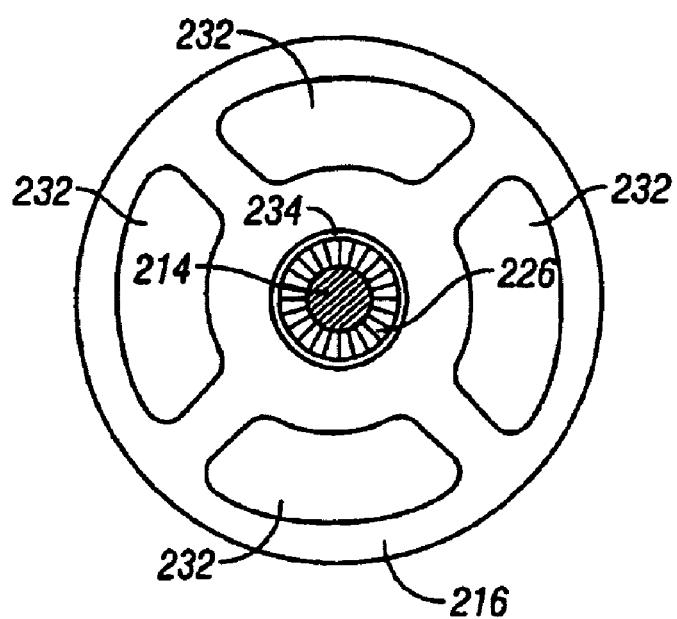

Referring now to FIGS. 8A–8C, a fourth embodiment of the insulation tube 216 is illustrated. In this embodiment, the separation may comprise a combination of air and low dielectric constant material. In particular, the insulation tube 216 forms a geometry that seals a plurality of sectors of air 232 around the conductor 214. These four cross-sectional quadrants of air 232, as shown in FIGS. 8B and 8C, in combination with the low dielectric material provides for a reduction in capacitive coupling. Additionally, as shown in FIG. 8C, a concentric ring of air 234 is also sealed around the conductor.

Referring back to FIG. 4, the electrocautery end effector 210 for delivering electrical energy to treatment tissue may be releasably mountable on an associated pulley arrangement 218 to enable interchanging with other end effectors, e.g., cautery hook, scalpel, blade, scissor, grasper, clamp, stapler, and the like. Using the instrument 200 in such a universal manner reduces the number of instruments and the cost to a user. As illustrated, the end effector comprises an electrode 210. The conductor 214 for delivering electrical energy to tissue engaged by the end effector 210 extends from the interface 212 to the end effector 210. Typically, the conductor 214 terminates at a conductive seat or sleeve provided on the pulley arrangement 218, as illustrated in FIG. 4, to provide an electrical connection to the electrode 210. Optionally, the conductor 214 may terminate on a distal end of the shaft.

The pulley arrangement 218 forms part of a wrist mechanism generally indicated by reference numeral 236. The wrist mechanism has a single pulley arrangement 238. It will be appreciated that at least a portion of the wrist mechanism 236, preferably a distal portion 240, is formed from natural ULTEM™ material or a fluoropolymer so as to inhibit wrist surface conduction. In particular, a fluoropolymer is a preferred non-conductive material because of its improved hydrophobic properties and natural ULTEM™ material is a second preferred material due to a lack of added carbon as compared to black ULTEM™ material. As such, undesirable high voltage current that may creep from the conducting electrode 210 to an exterior surface of the exposed wrist member 236 causing wrist surface conduction will be inhibited by the non-conducting natural ULTEM™ material wrist thereby minimizing unintended burning of the patient and/or melting of the wrist mechanism. It will further be appreciated that the pulley arrangement 218 and a member 242 defining a clevis which is mounted on the distal end 206 of the shaft 202 are also typically made from non-conductive plastics such as polyethermide or ULTEM™ material. Cables 244 extending internally along the shaft 202 also have non-conductive portions. Moreover, any further capacitive conduction leakage from the conductor 214 to the cables 244 in the main shaft 202 is inhibited by the increased dielectric resistance posed by the insulation tube 216 and separation 217 of the present invention. As such, any capacitive coupling between exposed cables 244 at the wrist 236, 242 and a patient is minimized.

The surgical instrument interface 212 may further comprise an electrical connector 220 for connecting the conductor 214 to an external electrosurgical generator (not shown). The connector 220 is typically a conventional banana-type plug. The interface housing is typically of a non-conductive material. In use, the patient is earthed and a voltage is supplied to the electrode 210. Electrical energy may be supplied to the surgical instrument 200 of the present invention by a conventional electrosurgical generator, such as the model Force 2 Electrosurgical Generator and related models made by Valley Lab of Boulder, Colo. The surgeon may activate an input, such as a foot switch electrically connected to the electrosurgical generator, causing the generator to supply electrical energy through a power cord and the connector 220 to the instrument 200. Typically a high frequency AC or RF current may be employed, with the voltage being dependent on the type and degree of treatment desired. Voltages may range up to at least 12,000V in some cases, with about 3000V being a typical value, e.g., for coagulation.

Hence, delivering electrical energy comprises transmitting electrical energy to the end effector 210 from the conductor 214 by connecting the external electrosurgical generator to the conductor 214 via plug 220. The delivered electrical energy produces heat capable of treating the tissue. For example, the heat may cauterize the tissue or coagulate blood so as to minimize bleeding during a treatment procedure. Preferably, electrical energy delivery is carried out in a monopolar fashion, although in certain circumstances, the principles of the present invention may be modified to include alternative instruments having bipolar electrodes. Monopolar and bipolar devices may use radio frequency (RF) energy to provide the heat necessary for cauterization and coagulation. Monopolar devices are typically used in conjunction with a grounding pad wherein one pole of the electrosurgical generator is mounted to the instrument and other pole is mounted to the grounding pad. The electrical current in monopolar devices travels from the instrument through the patient's body to the grounding pad. Bipolar instruments are typically connected to both poles of the electrosurgical generator. Current flow in bipolar devices is typically limited to tissue adjacent to the working end of the bipolar instrument.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A surgical instrument for use with a robotic surgical system, the instrument comprising:

an elongate shaft having a proximal end and a distal end and defining an internal longitudinally extending passage;

an electrocautery end effector disposed at the distal end of the shaft;

an interface disposed at the proximal end of the shaft, the interface removably connectable to the robotic surgical system;

a conductor extending from the interface to the end effector so as to deliver electrical energy to tissue engaged by the end effector, an insulation tube extending within the passage and over the conductor; and at least two o-rings disposed within the insulation tube so as to seal the insulation tube at each of its ends while centering the conductor within insulation tube, wherein an interior of the insulation tube between the sealed ends is filled with a filler material down to the conductor so as to inhibit capacitive coupling between the shaft and a surgical patient.

2. A surgical instrument as in claim 1, wherein the electrical energy is monopolar.

3. A surgical instrument as in claim 2, wherein the capacitive coupling is reduced by the insulation tube and separation by about 40% to about 75% over a similar instrument lacking the insulation tube and separation.

4. A surgical instrument as in claim 2, wherein current leakage between the shaft and the patient is limited to a range from about 20 mA to about 35 mA.

5. A surgical instrument as in claim 1, wherein the filler material comprises a low dielectric constant material.

6. A surgical instrument as in claim 5, wherein the low dielectric constant material and the sealed insulation tube form an integrated unit.

7. A surgical instrument as in claim 5, wherein the low dielectric constant material is fluorinated ethylene propylene, polyimide, silicone, polytetrafluoroethylene, tetrafluoroethylene, perfluoroalkoxy, ethylene tetrafluoroethylene, polypropylene, or a combination thereof.

8. A surgical instrument as in claim 1, wherein the insulation tube comprises a hypotube having a generally circular cross-section.

9. A surgical instrument as in claim 1, wherein the insulation tube has an outer diameter in the range from 1/16 inch to 3/16 inch.

10. A surgical instrument as in claim 1, wherein the insulation tube has a length in the range from 12 inches to 18 inches.

11. A surgical instrument as in claim 1, wherein the insulation tube is firmed from fluorinated ethylene propylene, polyimide, silicone, polytetrafluoroethylene, tetrafluoroethylene, perfluoroalkoxy, ethylene tetrafluoroethylene, polypropylene, or a combination thereof.

12. A surgical instrument as in claim 1, wherein a radial distance of the conductor from the insulation tube is in the range from 1/64 inch to 3/32 inch.

13. A surgical instrument as in claim 1, wherein the at least two o-rings comprise two pairs of o-rings, a first pair positioned at a proximal end of the insulation tube and a second pair positioned at a distal end of the insulation tube.

14. A surgical instrument as in claim 1, wherein the sealed insulation tube has a pressure threshold range from about −15 psi to 30 psi.

15. A surgical instrument as in claim 1, further comprising an insulative sheath disposed over the conductor.

16. A surgical instrument as in claim 1, wherein the elongate shaft comprises or is covered with an insulating material.

17. A surgical instrument as in claim 1, wherein the electrocautery end effector and at least the distal end of the shaft are insertable and retractable through a minimally invasive surgical incision.

18. A surgical instrument as in claim 1, wherein the electrocautery end effector comprises an electrode.

19. A surgical instrument as in claim 1, wherein the interface further comprises an electrical connector for connecting the conductor to an external electrosurgical generator.

20. A surgical instrument as in claim 1, further comprising a wrist member defining an end effector pivot and a wrist pivot spaced apart from the end effector pivot, the end effector being pivotally connected at the end effector pivot and the wrist member being pivotally mounted on the distal end of the shaft by means of the wrist pivot to be angularly displaceable relative to the shaft about a wrist pivot axis defined by the wrist pivot.

21. A surgical instrument as in claim 1, further comprising a wrist member including a movable portion coupleable to the end effector and to the distal end of the shaft, the movable portion being actuatable to move the end effector in at least one degree of freedom relative to the shaft.

22. A surgical instrument as in claim 21, wherein the movable portion includes a plurality of pivotally coupled segments.

23. A surgical instrument as in claim 21, wherein the movable portion includes at least one resilient element coupling the end effector to the distal end of the shaft.

24. A surgical instrument as in any one of claims 20–23, wherein at least a portion of the wrist member is formed from a polymeric material or a fluoropolymer so as to inhibit wrist surface conduction.

25. A surgical instrument for use with a robotic surgical system, the instrument comprising: an elongate shaft having a proximal end and a distal end and defining an internal longitudinally extending passage, the distal end of the shaft being configured to permit insertion through a minimally invasive incision in a body of a patient; an electrocautery end effector disposed at the distal end of the shaft; an interface disposed at the proximal end of the shaft, the interface removably connectable to the robotic surgical system; a conductor extending from the interface and electrically communicating with at least a portion of the end effector so as to deliver electrical energy to tissue engaged by the end effector; an insulative sleeve disposed over the conductor; an insulation tube extending within the passage and over the insulated conductor, wherein a separation is maintained between the sealed insulation tube and the insulated conductor; and at least two o-rings disposed within the insulation tube so as to seal the insulation tube at each of its ends while centering the conductor within the insulation tube, wherein an interior of the insulation tube between the seated ends is filled with a filler material down to the conductor so as to inhibit capacitive coupling between the shaft and a surgical patient.

26. An electrosurgical instrument, the instrument comprising: an elongate shaft having a proximal end and a distal end and defining an internal longitudinally extending passage; an electrocautery end effector disposed at the distal end of the shaft, wherein at least the end effector and distal end of the shaft are configured to be insertable through a minimally invasive surgical incision; a user-controllable interface disposed at the proximal end of the shaft; a conductor extending from the interface to the end effector so as to deliver electrical energy to tissue engaged by the end effector; an insulation tube extending within the passage and over the conductor; and at least two o-rings disposed within the insulation tube so as to seal the insulation tube at each of its ends while centering the conductor within the insulation tube, wherein an interior of the insulation tube between the sealed ends is filled with a filler material down to the conductor so as to inhibit capacitive coupling between the shaft and surgical patient.

27. An electrosurgical instrument as in claim 26, wherein the user-controllable interface is configured to couple to a manually movable handle.

28. An electrosurgical instrument as in claim 26, wherein the user-controllable interface is configured to removably couple to a servomechanical tool holder of a robotic surgical system.

* * * * *